(12) United States Patent
Smith et al.

(10) Patent No.: US 8,152,762 B2
(45) Date of Patent: Apr. 10, 2012

(54) PLUNGER ACTIVATED VACUUM RELEASE MECHANISM FOR A SYRINGE

(75) Inventors: Jeffrey Smith, Irvine, CA (US); Rex O. Bare, Lake Forest, CA (US); Daniel Thayer, Mission Viejo, CA (US)

(73) Assignee: SafeShot Technologies, LLC, Mission Viejo, CA (US)

( * ) Notice: Subject to any disclaimer, the term of this patent is extended or adjusted under 35 U.S.C. 154(b) by 0 days.

(21) Appl. No.: 11/784,796

(22) Filed: Apr. 10, 2007

(65) Prior Publication Data

US 2007/0255212 A1  Nov. 1, 2007

Related U.S. Application Data (60) Provisional application No. 60/793,383, filed on Apr. 20, 2006.

(51) Int. Cl.
*A61M 5/00* (2006.01)
(52) U.S. Cl. ......... 604/110; 604/111; 604/195; 604/198
(58) Field of Classification Search .......... 604/192–198, 604/110, 111, 156
See application file for complete search history.

(56) References Cited

U.S. PATENT DOCUMENTS

| | | | |
|---|---|---|---|
| 4,766,908 A | 8/1988 | Clement | |
| 4,838,869 A | 6/1989 | Allard et al. | |
| 4,950,241 A | 8/1990 | Ranford | |
| 4,966,593 A | 10/1990 | Lennox | |
| 4,973,308 A * | 11/1990 | Borras et al. | 604/110 |
| 5,019,043 A | 5/1991 | Segui Pastor et al. | |
| 5,085,640 A | 2/1992 | Gibbs | |
| 5,195,985 A | 3/1993 | Hall | |
| 5,211,630 A | 5/1993 | Schmahmann | |
| 5,215,015 A | 6/1993 | Iida et al. | |
| 5,215,533 A | 6/1993 | Robb | |
| 5,226,893 A | 7/1993 | Kayser | |
| 5,334,155 A | 8/1994 | Sobel | |
| 5,336,185 A | 8/1994 | Lynch et al. | |
| 5,344,403 A | 9/1994 | Lee | |
| 5,385,551 A | 1/1995 | Shaw | |
| 5,389,076 A | 2/1995 | Shaw | |
| 5,423,758 A | 6/1995 | Shaw | |

(Continued)

FOREIGN PATENT DOCUMENTS

EP  0 668 085 A2  8/1995

(Continued)

*Primary Examiner* — Bhisma Mehta
*Assistant Examiner* — Larry R Wilson
(74) *Attorney, Agent, or Firm* — K&L Gates LLP (57) ABSTRACT

A retractable safety syringe may comprise a needle, needle holder, syringe body, and a plunger. A proximal portion of the body and a piston of the plunger may define a variable vacuum compartment. A through hole pneumatically connecting ambient air and the variable vacuum compartment may be formed through a thumb platform and rigid shaft of the plunger for allowing air to escape out of the variable vacuum compartment when a piston of the plunger is traversed toward the retracted position and allow air to be introduced into the variable vacuum compartment when the piston is traversed toward the engaged position. A retraction force may be created by the variable vacuum compartment by covering an entrance of the through hole and traversing the piston to the engaged position. At the engaged position, the piston may engage the needle holder and the retraction force may retract the piston, needle holder and needle into the syringe body to prevent accidental needle pricking and needle reuse.

20 Claims, 5 Drawing Sheets

U.S. PATENT DOCUMENTS

| | | |
|---|---|---|
| 5,578,011 A | 11/1996 | Shaw |
| 5,578,015 A | 11/1996 | Robb |
| 5,601,534 A | 2/1997 | Turner |
| 5,632,733 A | 5/1997 | Shaw |
| 5,658,257 A | 8/1997 | Ryles |
| 5,681,292 A | 10/1997 | Tober et al. |
| 5,868,713 A | 2/1999 | Klippenstein |
| 5,964,735 A | 10/1999 | Alexander |
| 5,971,964 A | 10/1999 | Donaldson |
| 6,010,486 A | 1/2000 | Carter et al. |
| 6,015,438 A | 1/2000 | Shaw |
| 6,033,385 A | 3/2000 | Liu |
| 6,036,674 A | 3/2000 | Caizza et al. |
| 6,050,977 A | 4/2000 | Adams |
| 6,090,077 A | 7/2000 | Shaw |
| 6,193,695 B1 * | 2/2001 | Rippstein, Jr. ............... 604/195 |
| 6,368,303 B1 | 4/2002 | Caizza |
| 6,413,236 B1 * | 7/2002 | Van Dyke .................... 604/110 |
| 6,458,105 B1 * | 10/2002 | Rippstein et al. ............ 604/195 |
| 6,632,198 B2 | 10/2003 | Caizza |
| 6,712,787 B1 | 3/2004 | Dysarz |
| 6,840,291 B2 | 1/2005 | Caizza et al. |
| 6,953,449 B2 | 10/2005 | Huang |
| 6,986,756 B2 | 1/2006 | Pelkey et al. |
| 7,104,970 B2 | 9/2006 | Chen |
| 7,118,552 B2 | 10/2006 | Shaw et al. |
| 7,147,621 B2 | 12/2006 | Kiehne |
| 7,220,247 B2 | 5/2007 | Shaw et al. |
| 2001/0053886 A1 | 12/2001 | Caizza |
| 2002/0193736 A1 | 12/2002 | Kiehne |
| 2003/0023205 A1 | 1/2003 | Botich et al. |
| 2003/0212362 A1 | 11/2003 | Roser |
| 2004/0024357 A1 | 2/2004 | Pelkey et al. |
| 2004/0116857 A1 | 6/2004 | Kiehne |
| 2006/0089593 A1 | 4/2006 | Landau et al. |
| 2006/0089594 A1 | 4/2006 | Landau |
| 2006/0178625 A1 | 8/2006 | Lim et al. |
| 2008/0221517 A1 * | 9/2008 | Shaw et al. .................... 604/110 |

FOREIGN PATENT DOCUMENTS

EP         0668085 A2 *    8/1995

* cited by examiner

PLUNGER ACTIVATED VACUUM RELEASE MECHANISM FOR A SYRINGE

CROSS-REFERENCE TO RELATED APPLICATIONS

This application claims the benefits of U.S. Provisional Application No. 60/793,383, filed on Apr. 20, 2006, the entire content of which is incorporated herein by reference.

STATEMENT RE: FEDERALLY SPONSORED RESEARCH/DEVELOPMENT

Not Applicable

BACKGROUND

The present invention relates to a safety syringe.

In recent years, the public (e.g., drug addicts, drug users, medical personnel and healthcare providers and the like) has become increasingly aware of the health hazards associated with needle reuse and accidental needle prickings. For example, at least twenty blood-borne pathogens may be transmitted by the reuse of needles or accidental needle prickings. For example, Human Immunodeficiency Virus (HIV), Acquired Immunodeficiency Syndrome (AIDS), Hepatitis B, Hepatitis C, syphilis, malaria, tuberculosis, and herpes. Despite the awareness of the risk of needle reuse and accidental needle prickings, at least 36 percent of HIV/AIDS cases and more than 50 percent of Hepatitis B and Hepatitis C cases in the United States may be linked to the sharing of needles among drug addicts. Accordingly, there is a need to curb the practice of sharing needles among drug addicts.

The problem of needle sharing or needle reuses is further amplified when viewed in relation to the world population. For example, approximately 30 percent of reported HIV/AIDS cases in Brazil, Chile, Uruguay, Paraguay and Argentina are directly related to the sharing of contaminated needles among drug addicts. Approximately 70 percent of the HIV cases reported in China are directly linked to the sharing of contaminated needles. In eastern European countries, 80 percent of injection drug addicts admit to sharing contaminated needles. Approximately 43 percent of HIV/AIDS cases reported in Poland and Yugoslavia are linked to the sharing of contaminated needles among drug addicts.

Accidental needle prickings also pose a threat to healthcare workers. In particular, approximately one million accidental needle prickings are reported by healthcare workers annually. However, it is believed that at least three million accidental needle prickings occur each year, of which about two million are unreported. Various studies estimate that out of all the accidental needle pricking injuries that occur to nurses, approximately 40 percent to 53 percent go unreported. Various studies also estimate that out of all the needle pricking injuries that occur to laboratory technicians, approximately 92 percent go unreported. Various studies further estimate that out of all the needle pricking injuries that occur to physicians, approximately 70 percent to 95 percent go unreported.

In 1997, the Center for Disease Control and Prevention (CDC) sponsored a study which found that approximately 76 percent of needle pricking injuries could be avoided by using safety needles. Presently, there are at least 250 types of safety syringes. Unfortunately, the safety syringes that currently exist have been criticized for various problems associated in operating the safety syringe and its ineffectiveness.

One type of safety syringe is a vacuum assisted retractable safety syringe. One issue with the vacuum assisted retractable safety syringe is that after fluidic medication is filled within a variable fluid chamber and trapped air within the variable fluid chamber is ejected therefrom, the user or medical professional must not remove thumb pressure from a thumb platform. Otherwise, air will be reintroduced into the variable fluid chamber which is an unacceptable result. Such possibility increases the health risk to patients and liability to doctors and hospitals.

Accordingly, there is a need in the art for an improved safety syringe.

BRIEF SUMMARY

The safety syringe discussed herein addresses the needs discussed above, below and those that are known in the art.

The safety syringe may have a syringe body and a plunger which extends through a proximal portion of the syringe body. The plunger may have a thumb platform, rigid shaft and piston. The piston may be disposed within the syringe body along with a portion of the rigid shaft. Also, the thumb platform is disposed external to the syringe body along with a portion of the rigid shaft. Traversal of the thumb platform toward or away from the syringe body may traverse the piston toward an engaged position or a retracted position, respectively. The piston, syringe body and the proximal portion of the syringe body may define a variable vacuum compartment. A through hole may be formed through the thumb platform and the rigid shaft. Also, an air outlet may be formed through the rigid shaft connecting the variable vacuum compartment and the through hole. The air outlet and the through hole provide air communication between the variable vacuum compartment and the environment. The through hole and air outlet permit air to be introduced into the variable vacuum compartment when the piston is traversed from the retracted position toward the engaged position. Conversely, the through hole and air outlet permit air from within the variable vacuum compartment to escape from the variable vacuum compartment to the environment via the through hole and air outlet when the piston is traversed toward the retracted position.

A variable fluid chamber is defined by the piston, needle holder and syringe body. The variable vacuum compartment and variable fluid chamber vary inversely with respect to each other when fluidic medication is being filled in the variable fluid chamber and when fluidic medication is being injected into a patient.

During operation of the safety syringe, the through hole and air outlet may be unimpeded or unrestricted thereby permitting air to be introduced into or removed from the variable vacuum compartment. After fluidic medication is filled within the variable fluid chamber and any air trapped within the variable fluid chamber removed therefrom, the user or medical professional blocks airflow through the through hole. By way of example and not limitation, air flow through the through hole may be blocked when the user places his or her thumb over an entrance of the through hole at the thumb platform. Since the user presses on the thumb platform to traverse the piston from the retracted position toward the engaged position, a seal is formed between the thumb platform and the thumb. No air is introduced into the variable vacuum compartment. The variable vacuum compartment produces or creates a retraction force which urges the piston back toward the retracted position. When the piston has been traversed to the engaged position, the piston engages the needle holder and needle. The user maintains thumb pressure on the thumb platform but reduces the thumb pressure to a level lower than the retraction force of the variable vacuum compartment. The piston along with the needle holder and needle are retracted into the syringe body via the retraction force. When the needle is entirely retracted into the syringe body, the needle cannot accidentally prick the medical professional, user or another person. Also, the needle may not be reused. Hence, the used syringe may be safely discarded.

Alternatively, instead of blocking airflow through the through hole by placing the thumb over the entrance of the through hole, a shut off valve may be closed. The shut off valve may be located on the proximal portion of the plunger. In particular, the shut off valve may comprise a slot formed in the thumb platform and a vane sized and configured to be slideably received into the slot. The vane may have a hole which is aligned to the through hole when the vane is in an opened position. The vane may be traversed to a closed position which misaligns the hole of the vane and the through hole of the plunger to block passage of air through the through hole.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
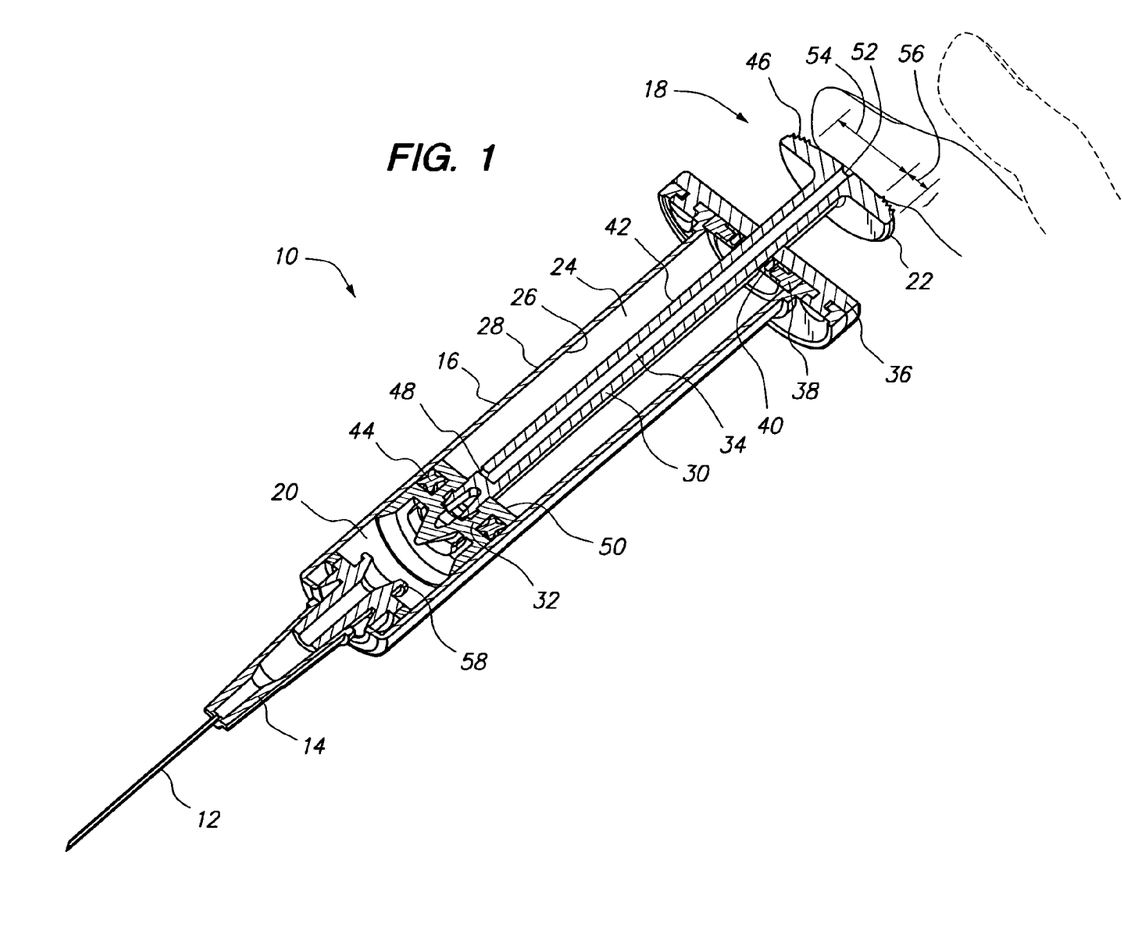
FIG. 1 is a cross sectional perspective view of a retractable safety syringe with a through hole providing air communication between a variable vacuum compartment and the environment.

Referring now to the drawings which are for the purposes of illustrating preferred embodiments of the safety syringe 10 and not for the purpose of limiting the same, FIG. 1 is a front cross-sectional view of the safety syringe 10. The safety syringe 10 may have a needle 12, needle holder 14, body 16 and a plunger 18 which cooperate with each other to permit medical professionals or users to inject themselves or others (e.g., patients, etc.) with fluidic medication. Moreover, the safety syringe 10 may automatically retract the needle 12 and needle holder 14 into the body 16 (see FIG. 4) after the safety syringe 10 has been used to inject the patient with the fluidic medication to prevent or mitigate against accidental needle pricking and needle reuse. In particular, the safety syringe 10 may define a variable fluid chamber 20 fillable with fluidic medication. To inject the patient with the fluidic medication, the plunger 18 may be traversed from a retracted position (defined below) toward an engaged position (see FIG. 3). As the plunger 18 is traversed toward the engaged position, fluidic medication is transferred from the variable fluid chamber 20 to the patient. When the plunger 18 has reached the engaged position, the plunger 18 may engage the needle holder 14 and needle 12. The medical professional may maintain thumb pressure on a thumb platform 22 but reduce the thumb pressure to a level below a retraction force of a variable vacuum compartment 24. The retraction force created by the variable vacuum compartment 24 of the safety syringe 10 may retract the plunger 18 to the retracted position and draw the needle 12 and needle holder 14 into the body 16 of the safety syringe 10. Accordingly, after use, the safety syringe 10 prevents accidental needle pricking and reuse of the safety syringe 10.

The syringe body 16 may have an elongate cylindrical configuration defining an inner surface 26 and an outer surface 28. The plunger 18 may comprise the thumb platform 22, rigid shaft 30 and a piston 32 which may be rigidly fixed to each other. The piston 32 and a portion of the rigid shaft 30 may be disposed within the syringe body 16. Also, a portion of the rigid shaft 30 and the thumb platform 22 may be disposed externally from the syringe body 16 at a proximal portion of the syringe body 16. The rigid shaft 30 may extend from within the syringe body 16 through a proximal portion of the syringe body 16. The piston's position within the syringe body 16 may be traversed by pushing and pulling the thumb platform 22 toward and away from the proximal portion of the syringe body 16. In particular, the piston 32 may be traversable between the retracted position and the engaged position. Generally, the retracted position is when the piston 32 is closer to the proximal portion of the syringe body 16 than the distal portion of the syringe body 16. But, the retracted position may include situations when the piston 32 does not contact the needle holder 14 and the piston 32 is closer to the distal portion of the syringe body 16 than the proximal portion of the body 16. The engaged position is when the piston 32 is in contact with the needle holder 14 and engaged to the needle holder 14 (see FIG. 3).

Initially, the safety syringe 10 may be provided to a medical professional or user with the piston 32 in a filling position without fluidic medication contained within the variable fluid chamber 20. The filling position is when the piston 32 is between the engaged position and the retracted position and closely adjacent the needle holder 14. By way of example and not limitation, the filling position may be when the piston 32 is closely adjacent to the needle holder 14 than the proximal portion of the syringe body 16 or in contact with the needle holder 14 but not engaged to the needle holder 14. To traverse the piston 32 from the filling position to the retracted position, the medical professional or user may pull the thumb platform 22 away from the proximal portion of the syringe body 16 by placing his or her first and second fingers underneath the thumb platform 22 and pushing the syringe body 16 by grasping the outer surface 28 of the syringe body 16. Please note that air is introduced into the variable vacuum compartment 24 through a through hole 34. When the piston 32 is traversed toward the retracted position from the filling position, the thumb is not in contact with the thumb platform 22 as shown by the dashed thumb outline of FIG. 1. Also, no pressure is produced in the variable vacuum compartment 24. Conversely, to traverse the piston 32 from the retracted position to the extended position to inject medication into the patient, the user or medical professional may place his or her fingers underneath finger platforms 36 attached to the proximal portion of the syringe body 16 and depress the thumb platform 22 with his or her thumb. The thumb may block an entrance 52 of the through hole 34 such that air does not enter the variable vacuum compartment 24. When air is not permitted to flow through the through hole 34, a vacuum is produced within the variable vacuum compartment 24 which produces a retraction force that will retract the needle 12 into the body 16.

An attachment base 38 may also be attached to the proximal portion of the syringe body 16. An aperture may be formed through the attachment base 38 through which, the rigid shaft 30 may be traversed as the piston 32 is traversed between the retracted position and the engaged position. A first seal 40 may be disposed about an inner periphery of the aperture of the attachment base 38. The first seal 40 may form an airtight seal between the attachment base 38 and an outer surface 42 of the rigid shaft 30.

The piston 32 may have a second seal 44 which engages an outer surface of the piston 32 and the inner surface 26 of the syringe body 16. The second seal 44 may form a watertight seal and an airtight seal between the piston 32 and the inner surface 26 of the syringe body 16. The second seal 44 may traverse along the inner surface 26 of the syringe body 16 as the piston 32 is traversed between the retracted position and the engaged position.

The variable vacuum compartment 24 may be defined by the inner surface 26 of the syringe body 16, the piston 32 and the attachment base 38. The variable vacuum compartment 24 is larger when the piston 32 is in the engaged position compared to the retracted position. On the other side of the piston 32 is the variable fluid chamber 20 defined by the second seal 44, a needle holder 14 and inner surface 26 of the body 16. In contrast to the variable vacuum compartment 24, the variable fluid chamber 20 is typically largest when the piston 32 is in the retracted position than the engaged position. Accordingly, the volumes of the variable vacuum compartment 24 and the variable fluid chamber 20 vary inversely with respect to each other.

The needle holder 14 may be removeably attached to a distal portion of the syringe body 16. The needle holder 14 forms a watertight and airtight seal between the syringe body 16 and needle holder 14. Fluid may be introduced into the variable fluid chamber 20 via the needle 12. When fluid is introduced into the variable fluid chamber 20, fluid is not permitted to escape out of the variable fluid chamber 20 between the needle holder 14 and syringe body 16. Also, fluid is not permitted to enter the variable vacuum compartment 24 by bypassing the second seal 44. Rather, the second seal 44 prevents any fluid transfer from the variable fluid chamber 20 to the variable vacuum compartment 24. Also, the second seal 44 prevents any air from being transferred from within the variable vacuum compartment 24 into the variable fluid chamber 20.

The plunger 18 discussed above may have a through hole 34 formed through the thumb platform 22 and the rigid shaft 30. The through hole 34 may begin from an outer surface 46 of the thumb platform 22 and extend through a substantial length of the rigid shaft 30. The distal end of the through hole 34 may have an air outlet 48 which extends from the through hole 34 to the outer surface 42 of the rigid shaft 30. In this manner, ambient air may be permitted to enter the variable vacuum compartment 24 when the piston 32 is traversed from the retracted position to the engaged position. Also, air within the variable vacuum compartment 24 is permitted to escape to the environment when the piston 32 is retracted from the engaged position to the retracted position. The position of the air outlet 48 may be substantially closer to the piston 32 than the thumb platform 22 such that air may be introduced into or removed from the variable vacuum compartment 24 for a substantial distance while the piston 32 is traversed between the engaged position and the retracted position. Preferably, the air outlet 48 may abut a top surface 50 of the piston 32 such that air may be introduced into or removed from the variable vacuum compartment 24 along the entire length of the piston's traversal between the engaged position and the retracted position.

The entrance 52 of the through hole 34 at the thumb platform 22 may be positioned such that the medical professional or user's thumb may block the through hole's entrance 52 and restrict or impede any air from entering into the variable vacuum compartment 24 when the piston 32 is traversed from the retracted position toward the engaged position. The upper surface 46 of the thumb platform 22 may have a smooth surface and/or thumb conforming surface 54 such that there is an airtight seal between the medical professional or user's thumb and the upper surface 46 of the thumb platform 22. The thumb conforming surface 54 may surround the entrance 52 of the through hole 34. Outer peripheral surfaces 56 of the upper surface 46 of the thumb platform 22 may have a textured surface such that the thumb is less likely to slip off of the thumb platform 22 as the thumb applies pressure to the thumb platform 22 to traverse the piston 32 toward the engaged position. The seal between the medical professional or user's thumb and the smooth surface is further enhanced when the medical professional or user is wearing a latex glove. When the medical professional or user's thumb is disposed over the entrance 52 of the through hole 34 and the piston 32 is traversed from the retracted position toward the engaged position, no air is introduced into the variable vacuum compartment 24. Accordingly, the variable vacuum compartment 24 produces or creates a retraction force which urges the piston 32 back toward the retracted position as long as the user's thumb blocks air from being introduced into the variable vacuum compartment 24 via the through hole 34.

In use, the safety syringe 10 may be provided to the medical professional or user with the piston 32 in the filling position. The needle 12 of the safety syringe 10 may be inserted into a medication container containing fluidic medication. While the user or medical professional securely holds the medication container and the syringe body 16 in one hand, the medical professional or user may slip his or her fingers underneath the thumb platform 22 and pull the thumb platform 22 away from the syringe body 16. Note that the medical professional or user's thumb is not disposed over the entrance 52 of the through hole 34. As such, air within the variable vacuum compartment 24 is permitted to escape therefrom through the through hole 34. If air was not permitted to escape out of the variable vacuum compartment 24 through the through hole 34, then the piston 32 would compress the air within the variable vacuum compartment 24 and the variable vacuum compartment 24 would produce an extension force urging the piston 32 toward the engaged position or filling position. Fortunately, the through hole 34 is unimpeded or unrestricted thereby permitting air within the variable vacuum compartment 24 to escape out of the variable vacuum compartment 24 via the through hole 34.

As the piston 32 is traversed toward the retracted position, the fluid within the medication container is transferred into the variable fluid chamber 20 via the needle 12. When the appropriate amount of fluidic medication is filled in the variable fluid chamber 20, the user stops traversing the thumb platform 22 away from the syringe body 16. The user or medical professional removes the needle 12 from the medication container. A small amount of air may be trapped within the variable fluid chamber 20. To remove the trapped air, the user or medical professional may invert the safety syringe 10 such that the needle 12 is pointed upwardly. The user or medical professional taps the outside surface of the syringe body 16 to urge the trapped air within the variable fluid chamber 20 toward the needle tip. The medical professional or user may place his or her first and second fingers underneath the finger platforms 36 and place his or her thumb on the thumb platform 22 but not covering the entrance 52 of the through hole 34. The thumb may be placed on the thumb platform 22 adjacent the entrance 52 of the through hole 34. In this manner, when the thumb platform 22 is depressed to remove the trapped air within the variable fluid chamber 20, air is introduced into the variable vacuum compartment 24. No retraction force is created by the variable vacuum compartment 24 when the piston 32 is traversed toward the engaged position to remove trapped air within the variable fluid chamber 20. The thumb may be removed from the thumb platform and the piston will not be urged toward the retracted position.

At this moment, the safety syringe 10 has been prepared to inject the fluidic medication into a patient. The needle 12 is inserted into the patient and the piston 32 is traversed from the retracted position to the engaged position. The user or medical professional traverses the piston 32 from the retracted position to the engaged position by placing his or her first and second fingers under the finger platforms 36 and his or her thumb on the thumb platform 22 over the entrance 52 of the through hole 34 which restricts or impedes airflow through the through hole 34 as the piston 32 is traversed to the engaged position. Since no air is introduced into the variable vacuum compartment 24, the variable vacuum compartment 24 produces a retraction force which urges the piston 32 toward the retracted position. When the piston 32 is traversed to the engaged position, the piston 32 may engage the needle holder 14 and needle 12. Once the piston 32 engages the needle holder 14 and needle 12, the user or medical professional does not remove his or her thumb from the entrance 52 of the through hole 34. Rather, the user or medical professional may release pressure on the thumb platform 22 such that the retraction force is greater than the thumb pressure and the piston 32 is urged back toward the retracted position. The user or medical professional balances the thumb pressure applied to the thumb platform 22 and the retraction force to traverse the piston 32 back toward the retracted position and the needle 12 is retracted into the syringe body 16.

The piston 32 may be engageable to the needle holder 14 and needle 12 via any method known in the art. By way of example and not limitation, the piston 32 may be engageable to the needle holder 14 and needle 12 via the structure disclosed in U.S. Pat. No. 6,413,236, the entire content of which is expressly incorporated herein by reference.

Figure 2:
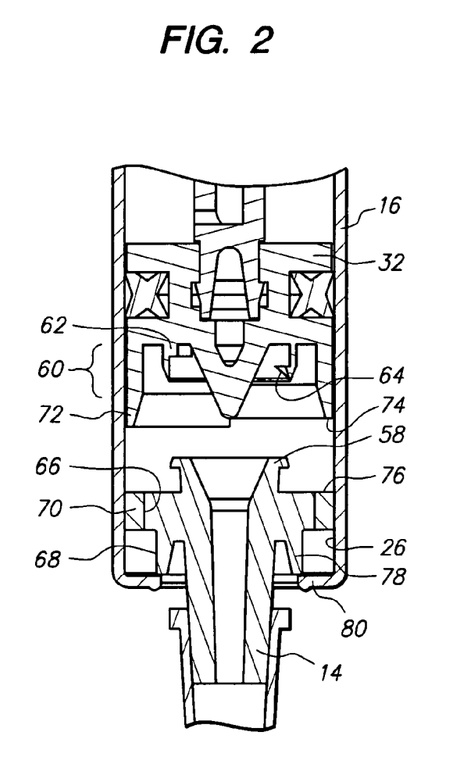
FIG. 2 is a front cross sectional view of a distal portion of the syringe with a piston disengaged to a needle holder.
Figure 3:
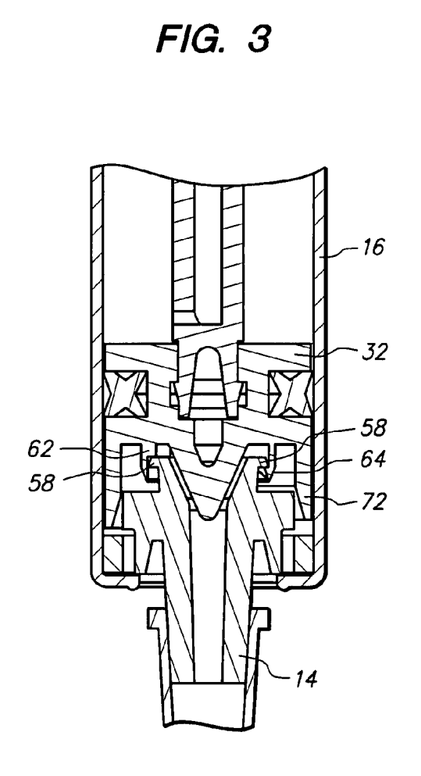
FIG. 3 is a front cross sectional view of the distal portion of the syringe with the piston engaged to the needle holder.
Figure 4:
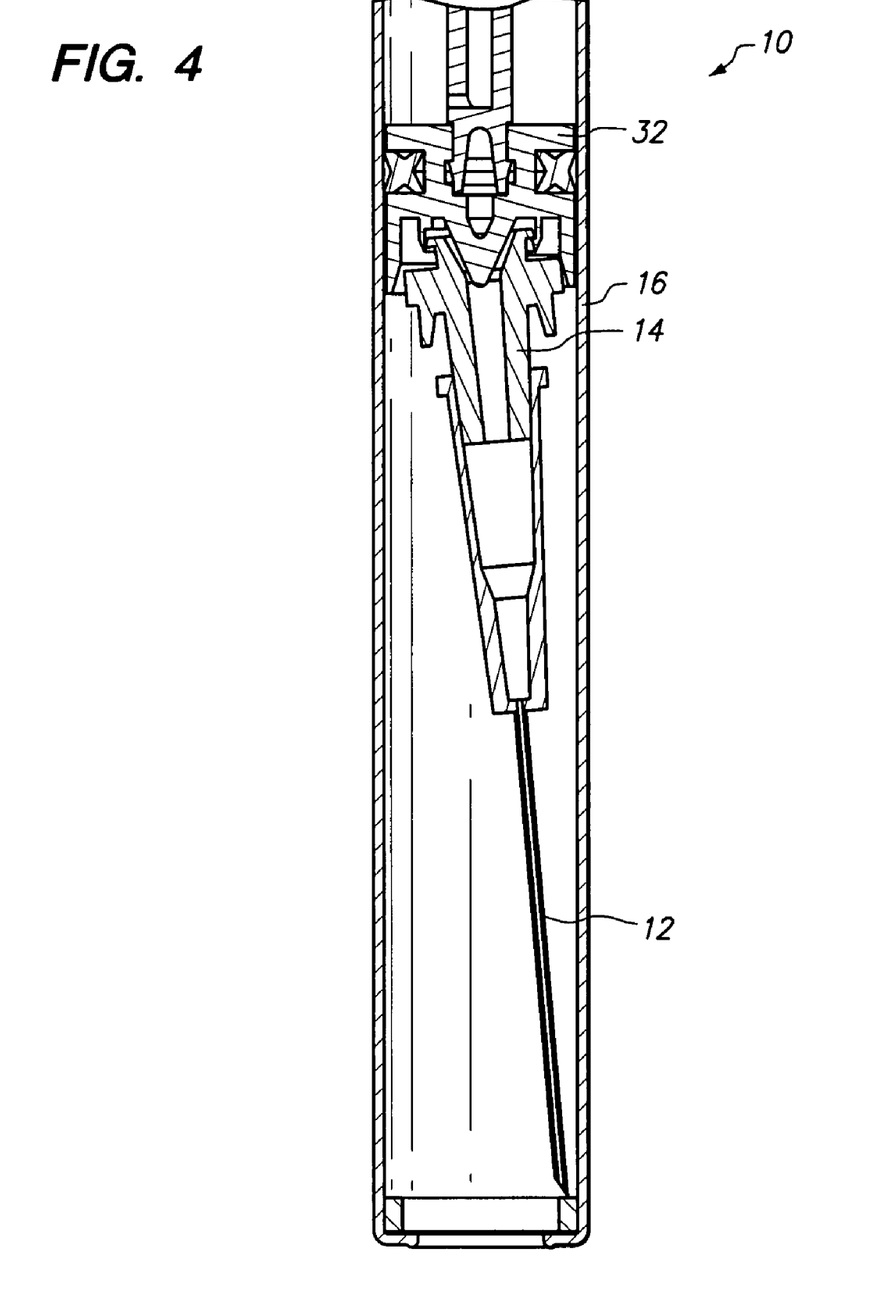
FIG. 4 is a partial cross sectional view of the syringe with a needle retracted into a body of the syringe.

Referring now to FIG. 2, by way of example and not limitation, the proximal portion of the needle holder 14 may have an outwardly directed flange 58. Also, the piston 32 may have longitudinal offset tabs 60 which engage the needle holder 14, and more particularly, the outwardly directed flange 58 of the needle holder 14. The longitudinal offset tabs 60 engages the outwardly directed flange 58 of the needle holder 14 such that when the piston 32 is withdrawn into the syringe body 16 via the retraction force, the needle 12 is also canted (see FIG. 4) toward one side of the syringe body 16. The longitudinal offset tabs 60 may comprise an upper proximal block tab 62 and a lower distal wedge tab 64. The lower distal wedge tab 64 passes and hooks onto the flange 58 of the needle holder 14 when the piston 32 is traversed to the engaged position, as shown in FIG. 3. The upper proximal block tab 62 does not pass the flange 58 of the needle holder 14 when the piston 32 is traversed to the engaged position. Rather, the upper proximal block tab 62 pushes down on the flange 58 of the needle holder 14. When the needle 12 and needle holder 14 are retracted into the syringe body 16, the upper proximal block tab 62 pushes down on the flange 58 of the needle holder 14 and the lower distal wedge tab 64 pulls up on the flange 58 of the needle holder 14 to cant the needle 12 to one side of the syringe, as shown in FIG. 4.

As stated above, the needle holder 14 may be engageable to the distal portion of the syringe body 16. In particular, the needle holder 14 may have a retaining surface 66 and a releasing surface 68, as shown in FIG. 2. The retaining surface 66 may be disposed immediately above the releasing surface 68. The retaining surface 66 may have an outer diameter which is larger than the releasing surface 68. Initially, when the needle holder 14 is engaged to the syringe body 16, a retaining member 70 may be interposed between the retaining surface 66 and the inner surface 26 of the syringe body 16. The retaining member 70 may frictionally engage the inner surface 26 of the syringe body 16 and may also frictionally engage the retaining surface 66 of the needle holder 14. The retaining member 70 may be disposed about the retaining surface 66 or the releasing surface 68. When the retaining member 70 is disposed about the retaining surface 66, the retaining member 70 is in a first position. Also, the needle holder 14 is engaged to the syringe body 16. When the retaining member 70 is disposed about the releasing surface 68, the retaining member 70 is in a second position. When the retaining member 70 is disposed about the releasing surface 68, the retaining member 70 may frictionally engage the inner surface 26 of the syringe body 16 but may be disengaged from the releasing surface 68. Also, the needle holder 14 may be disengaged from the syringe body 16 and retracted into the syringe body 16 under the retraction force of the variable vacuum compartment 24.

To traverse the retaining member 70 from the first position to the second position, the piston 32 may be formed with a punch 72. The punch 72 may be formed on the distal portion of the piston 32. The punch 72 may have a cylindrical configuration and be sized and configured to mate with the retaining member 70. More particularly, the punch 72 may have a lower surface 74 which mates with an upper surface 76 of the retaining member 70. When the piston 32 is traversed toward the engaged position, the lower surface 74 of the punch 72 contacts the upper surface 76 of the retaining member 70. When the piston 32 is further traversed to the engaged position, the punch 72 creates a force greater than the frictional forces between the retaining member 70 and the syringe body 16 and retaining surface 66 of the needle holder 14. The punch 72 of the piston 32 displaces the retaining member 70 from the first position to the second position. Also, a prong 78 contacts an inwardly directed flange 80 of the syringe body 16 to prevent the needle holder 14 from being pushed out of the syringe body 16. At about the moment that the retaining member 70 is traversed from the first position to the second position, the piston 32 engages the needle holder 14, as shown in FIG. 3.

Figure 5:
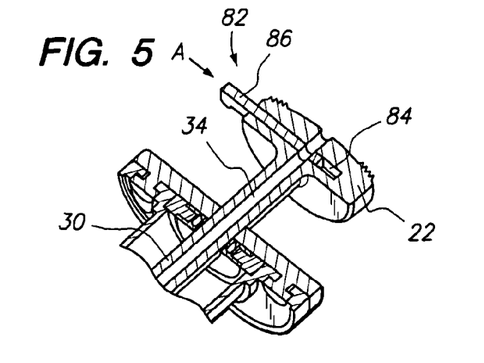
FIG. 5 is a partial cross sectional perspective view of a plunger with a shut off valve in an opened position to permit air to travel through the through hole.
Figures 6, 7, 8:
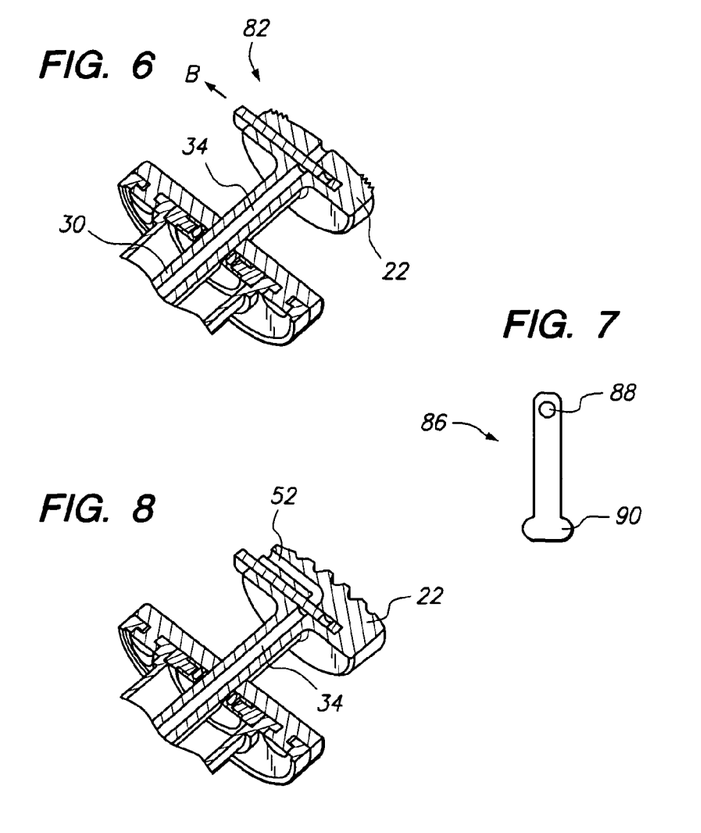
FIG. 6 is a partial cross sectional perspective view of the plunger with the shut off valve in a closed position to prevent air from traveling through the through hole.
FIG. 7 is a top view a vane of the shut off valve.
FIG. 8 is an alternate embodiment of the through hole wherein an entrance of the through hole is positioned on a side surface of a thumb platform.

Referring now to FIGS. 5-7, in another aspect of the safety syringe 10, the plunger 18 may have a shut off valve 82. The shut off valve 82 may have an opened position (see FIG. 5) and a closed position (see FIG. 6). In the opened position, air is permitted to flow through the through hole 34 to introduce air into the variable vacuum compartment 24 or remove air from the variable vacuum compartment 24. In the closed position, the shut off valve 82 blocks, impedes or restricts airflow through the through hole 34.

The thumb platform 22 may have a slot 84 formed transversely therethrough. The slot 84 may be sized and configured to receive a vane 86. The vane 86 may have an elongate flat configuration. A distal end of the vane 86 may have an aperture 88 (see FIG. 7) alignable to the through hole 34 when the shut off valve 82 is in the opened position. The vane 86 is also slideable within the slot 84 such that the aperture 88 of the vane 86 is mis-aligned with the through hole 34 when the shut off valve 82 is in the closed position. To traverse the vane 86 from the opened position to the closed position, the user may press a proximal portion of the vane 86 in the direction of arrow A shown in FIG. 5. Optionally, the vane 86 may be traversed back toward the opened position from the closed position by grasping tabs 90 at the proximal portion of the vane 86. In particular, the user may grasp the tabs 90 with his or her fingers to pull the vane 86 in direction B shown in FIG. 6.

In use, the safety syringe 10 with shut off valve 82 may be filled with fluidic medication and prepared for injection in the same manner discussed above. Just prior to injecting the fluidic medication into the patient, the user or medical professional depresses the proximal portion of the vane 86 so as to traverse the vane 86 from the opened position to the closed position. At this moment, air is not permitted to enter the variable vacuum compartment 24 or escape from the variable vacuum compartment 24 via the through hole 34. The user or medical professional inserts the needle 12 into the patient and applies thumb pressure to the thumb platform 22 so as to traverse the piston 32 from the retracted position toward the engaged position. Fluidic medication is injected into the patient. When the piston 32 has reached the engaged position, the needle holder 14 and piston 32 engages each other. Since no air was introduced into the variable vacuum compartment 24 while the piston 32 was traversed from the retracted position to the engaged position, the variable vacuum compartment 24 produces a retraction force urging the piston 32 from the engaged position back toward the retracted position.

The user may immediately release the thumb platform 22. The retraction force urges the piston 32, needle holder 14 and needle 12 back into the syringe body 16 thereby covering the needle 12 and preventing accidental needle prickings and needle reuse. Also, the needle 12 may be canted toward one side of the syringe body 16, as described above. Hence, the needle 12 is canted toward one side of the syringe body 16 such that the needle 12 cannot accidentally protrude through the distal end of the syringe body 16.

Alternatively, the entrance 52 of the through hole 34 may be positioned on a side of the thumb platform 22, as shown in FIG. 8, such that the thumb of the user or medical professional cannot block the through hole's entrance 52 when applying thumb pressure to the thumb platform 22. In this manner, the medical professional cannot inadvertently create a retraction force in the variable vacuum compartment 24 when the medical professional is clearing trapped air within the variable fluid chamber 20 just prior to injecting medication into the patient.

Figure 9:
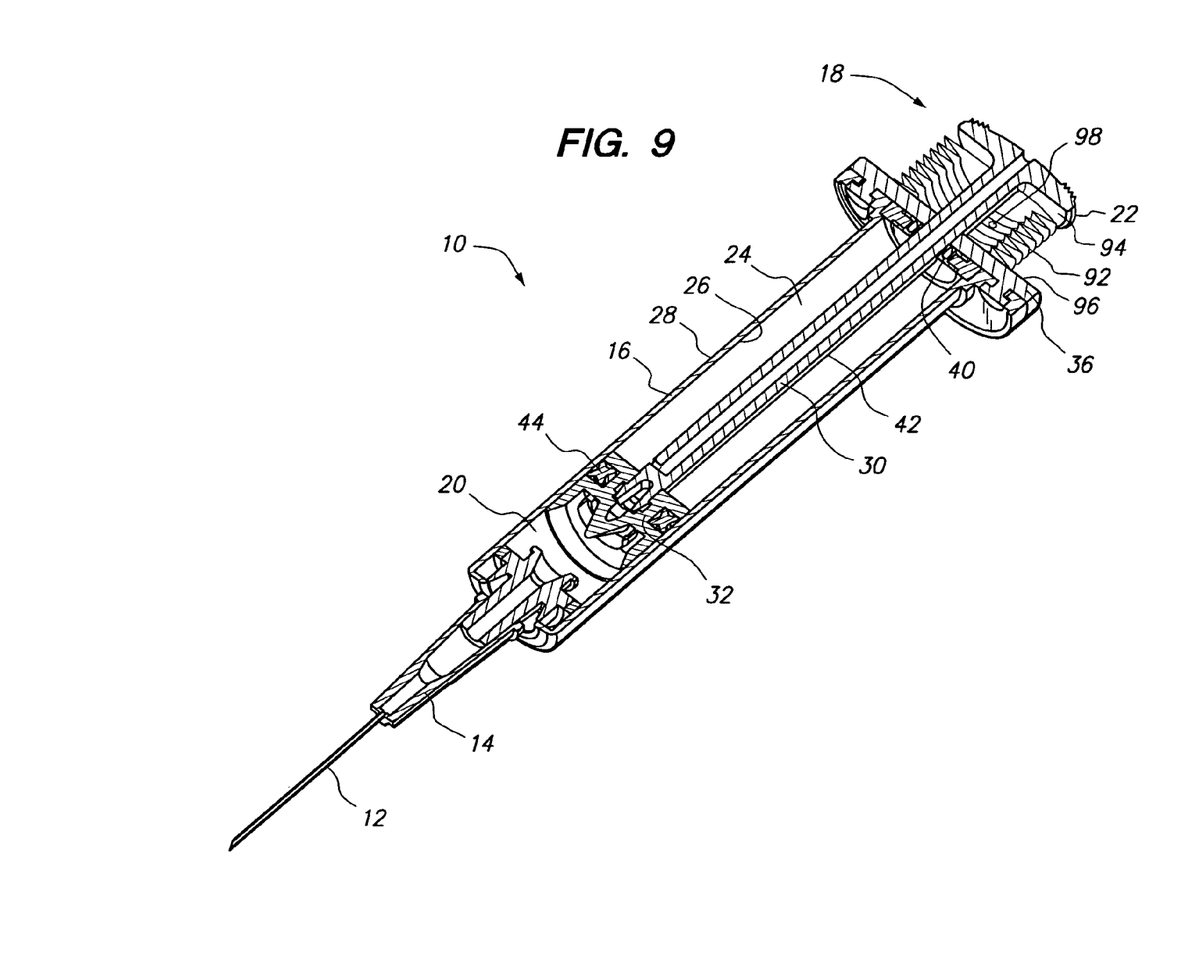
FIG. 9 is a front cross sectional perspective view of the syringe with a sheath disposed over a shaft of the plunger to prevent any contamination of the variable vacuum compartment and the variable fluid chamber.

The syringe 10 discussed herein provides for a sterile environment within the variable fluid chamber 20 such that fluidic medication filled within the variable fluid chamber 20 is not contaminated by the handling (e.g., touching outer surface 42 of plunger shaft 30) of the syringe 10 by the user or medical professional. The reason is that the first seal 40 is an airtight seal that prevents contaminates from entering the syringe body 16 (i.e., variable vacuum compartment 24) through its proximal portion. Moreover, the second seal 44 provides an additional barrier to prevent contaminates from entering the variable fluid chamber 20 through the proximal portion of the syringe body 16. To provide for an additional barrier to contamination, an optional sheath 92 may also be disposed over the proximal portion of the rigid shaft 30 of the plunger 18. The sheath 92 provides a physical barrier between the outer surface 42 of the shaft 30 and the medical professional's fingers such that during use of the syringe 10, no contact is made between the medical professional and the outer surface 42 of the shaft 30.

The sheath 92 may have an accordion configuration. The sheath 92 may expand longitudinally when the piston 32 is traversed toward the retracted position and contract when the piston 32 is traversed toward the engaged position. The sheath 92 may define a proximal portion and a distal portion. The proximal portion of the sheath 92 may be attached to a lower surface 94 of the thumb platform 22 via attachment methods known in the art such as adhesives, sonic welding, etc. The distal portion of the sheath 92 may be attached to an upper surface 96 of the finger platforms 36 via attachment methods known in the art such as adhesives, sonic welding, etc. The sheath 92 may have an air vent 98 to prevent compression of air within the sheath 92 when the thumb platform 22 is depressed and the piston 32 is traversed toward the engaged position. Air within the sheath 92 is permitted to escape out to the environment via the air vent 98. Also, the air vent 98 prevents a vacuum from forming within the sheath 92 when the thumb platform 22 is pulled out and the piston 32 is traversed toward the retracted position. Air from the environment is introduced into the sheath 92.

The sheath 92 prevents medical professionals from touching the outer surface 42 of the shaft 30 when operating the syringe 10. For example, the syringe 10 may be provided to medical professionals with the piston 32 in the retracted position. In the retracted position, the outer surface 42 of the shaft 30 is exposed and the medical professional may make contact with the medical professional when grasping the syringe 10. With the sheath 92 disposed over the proximal portion of the shaft 30, the medical professional cannot touch the outer surface 42 of the shaft 30. Accordingly, contaminates is further prevented from entering the variable fluid chamber 20 through the proximal portion of the syringe body 16.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A retractable safety needle syringe, the syringe comprising:
 a syringe body defining a distal end, a proximal portion and an inner surface;
 a variable fluid compartment located within the syringe body and in fluid communication with the distal end of the syringe, the variable fluid compartment configured to receive a liquid for injection into a patient through the distal end of the syringe;
 a variable vacuum compartment located proximally from the variable fluid compartment within the syringe body, the distal end of the variable vacuum compartment sealed on the distal end to prevent fluid communication from the variable vacuum compartment with the distal end of the syringe and with the variable liquid compartment, the variable vacuum compartment configured to produce a retraction force when the a plunger is depressed;

the plunger having
- a piston slideably disposed within the syringe body,
- a shaft extending through the proximal portion of the syringe body,
- a thumb platform attached to the shaft for traversing the piston between an engaged position and a retracted position, wherein the piston, the inner surface of the syringe body and the proximal portion of the syringe body define the variable vacuum compartment, and
- a through hole formed through the shaft, the through hole selectively blockable by a user independently of the position of the plunger within the syringe body, the through hole configured to provide air communication between the variable vacuum compartment and an environment external to the safety syringe when unblocked and to prevent air communication between the variable vacuum compartment and the environment when blocked, the variable vacuum compartment being otherwise sealed from the external environment;

a distal seal disposed between the plunger piston and the syringe body forming a fluid tight and air-tight seal between the plunger piston and the syringe body; and a needle holder disposable at the distal portion of the syringe body, the needle holder being removeably engageable to the distal portion of the syringe body and engageable to the piston;

wherein the vacuum compartment is configured to increase in volume when the piston moves toward the distal end of the syringe body, the increase in volume creating a retraction force when the through hole is blocked but not when the through hole is unblocked; and wherein the retraction force created is greater than a retaining force engaging the needle holder with the distal portion of the syringe body such that the retraction force moves the piston, the needle holder, and the needle toward the proximal portion of the syringe body when the injection is complete.

2. The syringe of claim 1 further comprising a proximal seal disposed between the plunger shaft and the syringe body forming an airtight seal between the plunger shaft and the syringe body, and wherein the proximal seal, distal seal and syringe body define the variable vacuum compartment.

3. The syringe of claim 1 wherein the through hole extends between an outer surface of the shaft and the thumb platform.

4. The syringe of claim 3 wherein an entrance of the through hole is centrally positioned on the thumb platform.

5. The syringe of claim 3 wherein an entrance of the through hole is laterally positioned on the thumb platform.

6. The syringe of claim 1 wherein the through hole is configured to be blocked by the placement of a finger over an entrance of the through hole.

7. The syringe of claim 1 further comprising a shut off valve configured to block the through hole.

8. The retractable safety syringe of claim 7, wherein the shutoff valve is located external to the syringe body.

9. The syringe of claim 1 wherein the through hole extends from a distal portion of the shaft to the thumb platform.

10. The retractable safety syringe of claim 1, wherein the through hole is selectively blockable externally to the syringe body.

11. A method of injecting fluid into a patient, the method comprising:

inverting a syringe having a needle attached to a needle holder so as to point the needle upward, the syringe having a tubular syringe body, a variable liquid compartment located within the syringe body and in fluid communication with the distal end of the syringe, the variable fluid compartment configured to receive a liquid for injection into a patient through the distal end of the syringe, a variable vacuum compartment located proximally from the variable liquid compartment within the syringe body, the distal end of the variable vacuum compartment sealed on the distal end to prevent fluid communication from the variable vacuum compartment with the distal end of the syringe and with the variable liquid compartment; a piston disposed within the syringe body forming a variable fluid chamber between the piston, the needle, and the inner surface of the syringe body, the syringe also containing a proximal seal disposed within the syringe body near a proximal end of the syringe body, the proximal seal, piston, and inner surface forming a variable vacuum compartment, a through hole selectively blockable by a user independently of the position of the plunger in the syringe body, the through hole passing from the interior of the variable vacuum compartment to the outside of the syringe, the through hole configured to provide air communication between the variable vacuum compartment and an environment external to the syringe when unblocked and to prevent air communication between the variable vacuum compartment and the environment when blocked, the variable vacuum compartment being otherwise sealed from the external environment;

leaving the through hole open while moving the piston of the syringe toward the needle to remove trapped air from the variable fluid chamber, allowing air into the variable vacuum compartment via the through hole to equalize pressure within the variable vacuum compartment with ambient pressure;

inserting the needle into the patient;

blocking the through hole while traversing the piston to inject a fluid into the patient, preventing air from entering the variable vacuum compartment and reducing the pressure within the variable vacuum compartment below the ambient pressure such that the variable vacuum compartment creates a retraction force while the through hole is blocked;

engaging the piston with the needle holder; and allowing the retraction force to move the piston, the needle holder, and the needle into the syringe body.

12. The method of claim 11 further comprising:

leaving the through hole open while moving the piston away from the needle, removing air from the variable vacuum compartment via the through hole while filling the variable fluid chamber with fluid.

13. The method of claim 11 wherein blocking the through hole further comprises placing one of a user's digits over an entrance of the through hole.

14. The method of claim 11 wherein blocking the through hole further comprises traversing a vane of a shut off valve from an open position to a closed position.

15. The method of claim 14, wherein the shutoff valve is located external to the syringe body.

16. The method of claim 11, wherein the through hole is blocked externally to the syringe body.

17. A retractable safety needle syringe, the syringe comprising:

a syringe body defining a distal end, a proximal portion and an inner surface;

a variable fluid compartment located within the syringe body and in fluid communication with the distal end of the syringe, the variable fluid compartment configured to receive a liquid for injection into a patient through the distal end of the syringe;

a variable vacuum compartment located proximally from the variable fluid compartment within the syringe body, the distal end of the variable vacuum compartment sealed on the distal end to prevent fluid communication from the variable vacuum compartment with the distal end of the syringe and with the variable liquid compartment, the variable vacuum compartment configured to produce a retraction force when the a plunger is depressed;

the plunger having
- a piston slideably disposed within the syringe body,
- a shaft extending through the proximal portion of the syringe body,
- a thumb platform attached to the shaft for traversing the piston between an engaged position and a retracted position, wherein the piston, the inner surface of the syringe body and the proximal portion of the syringe body define a the variable vacuum compartment, and
- a through hole formed through the shaft, the through hole selectively blockable by a user, the through hole configured to provide air communication between the variable vacuum compartment and an environment external to the safety syringe when unblocked and to prevent air communication between the variable vacuum compartment and the environment when blocked, the variable vacuum compartment being otherwise sealed from the external environment, so that, while the through hole is unblocked, air is introduced the variable vacuum compartment for a substantial distance while the plunger is traversed to an engaged position and air is removed from the variable vacuum compartment while the plunger is traversed to a retracted position;

a distal seal disposed between the plunger piston and the syringe body forming a fluid tight and air-tight seal between the plunger piston and the syringe body; and a needle holder disposable at the distal portion of the syringe body, the needle holder being removeably engageable to the distal portion of the syringe body and engageable to the piston;

wherein the vacuum compartment is configured to increase in volume when the piston moves toward the distal end of the syringe body, the increase in volume creating a retraction force when the through hole is blocked but not when the through hole is unblocked; and wherein the retraction force created is greater than a retaining force engaging the needle holder with the distal portion of the syringe body such that the retraction force moves the piston, the needle holder, and the needle toward the proximal portion of the syringe body when the injection is complete.

18. The syringe of claim 17 wherein the through hole extends between an outer surface of the shaft and the thumb platform.

19. The syringe of claim 18, wherein an entrance of the through hole is laterally positioned on the thumb platform.

20. The retractable safety syringe of claim 17, wherein the through hole is selectively blockable externally to the syringe body.

* * * * *